(12) United States Patent
Mirkin et al.

(10) Patent No.: US 7,824,473 B2
(45) Date of Patent: Nov. 2, 2010

(54) METAL-ORGANIC FRAMEWORK MATERIALS BASED ON ICOSAHEDRAL BORANES AND CARBORANES

(75) Inventors: Chad A. Mirkin, Wilmette, IL (US); Joseph T. Hupp, Northfield, IL (US); Omar K. Farha, Evanston, IL (US); Alexander M. Spokoyny, Evanston, IL (US); Karen L. Mulfort, Chicago, IL (US)

(73) Assignee: Northwestern University, Evanston, IL (US)

( * ) Notice: Subject to any disclaimer, the term of this patent is extended or adjusted under 35 U.S.C. 154(b) by 285 days.

(21) Appl. No.: 12/180,074

(22) Filed: Jul. 25, 2008

(65) Prior Publication Data
US 2009/0025556 A1    Jan. 29, 2009

Related U.S. Application Data

(60) Provisional application No. 60/962,195, filed on Jul. 27, 2007.

(51) Int. Cl.
*B01D 53/04* (2006.01)
*C08G 79/08* (2006.01)

(52) U.S. Cl. .................. 95/116; 95/900; 502/526; 528/4

(58) Field of Classification Search .............. 95/90, 95/116, 900, 902; 96/108; 423/248, 648.1, 423/658.2; 502/526; 206/0.7; 528/4
See application file for complete search history.

(56) References Cited

U.S. PATENT DOCUMENTS 5,648,508 A    7/1997    Yaghi

2003/0176396 A1*    9/2003    Shea et al. ............... 514/63
2009/0220400 A1*    9/2009    Farha et al. ............ 423/228

FOREIGN PATENT DOCUMENTS

| EP | 0200260 | 12/1986 |
|---|---|---|
| EP | 0389041 | 9/1990 |
| WO | WO-95/19222 | 7/1995 |

OTHER PUBLICATIONS

Bradshaw et al., "Design, chirality, and flexibility in nanoporous molecule-based materials", *Acc Chem Res*, 38:273-82 (2005).

Chen et al., "High $H_2$ adsorption in a microporous metal-organic framework with open metal sites", *Angew Chem Int Ed Engl*, 44:4745-9 (2005).

Cho et al., "A metal-organic framework material that functions as an enantioselective catalyst for olefin epoxidation", *Chem Commun (Camb)*, (24):2563-5 (2006).

Choi et al., "Dynamic and redox active pillared bilayer open framework: single-crystal-to-single-crystal transformations upon guest removal, guest exchange, and framework oxidation", *J Am Chem Soc*, 126:15844-51 (2004).

(Continued)

*Primary Examiner*—Frank M Lawrence
(74) *Attorney, Agent, or Firm*—Marshall, Gerstein & Borun LLP

(57) ABSTRACT

Disclosed herein are metal-organic frameworks of metals and boron rich ligands, such as carboranes and icosahedral boranes. Methods of synthesizing and using these materials in gas uptake are disclosed.

32 Claims, 6 Drawing Sheets

OTHER PUBLICATIONS

Czepirski et al., "Virial-type thermal equation of gas-solid adsorption", *J Chem Eng Sci*, 44:797-801 (1989).

Dinca et al., "Hydrogen storage in a microporous metal-organic framework with exposed $Mn^{2+}$ coordination sites", *J Am Chem Soc*, 128:16876-83 (2006).

Dinca et al., "Strong $H_2$ binding and selective gas adsorption within the microporous coordination solid $Mg_3(O_2C-C_{10}H_6-CO_2)_3$", *J Am Chem Soc*, 127:9376-9377 (2005).

El-Kaderi et al., "Designed synthesis of 3D covalent organic frameworks", *Science*, 316:268-72 (2007).

Evans et al., "Crystal engineering of nonlinear optical materials based on interpenetrated diamondoid coordination networks", *Chem Mater*, 13:2705-12 (2001).

Farha et al., "Synthesis and hydrogen sorption properties of carborane based metal-organic framework materials", *J Am Chem Soc*, 129:12680-1 (2007).

Gomez-Lor et al., "Novel 2D and 3D indium metal-organic frameworks: topology and catalytic properties", *Chem Mater*, 17: 2568-73 (2005).

Hawthorne, *Advances in Boron Chemistry*, Special Publication No. 201, Royal Society of Chemistry (London), 82:261 (1997).

Kitagawa et al., "Functional porous coordination polymers", *Angew Chem Int Ed Engl*, 43:2334-2375 (2004).

Kitaura et al., "Immobilization of a metallo schiff base into a microporous coordination polymer", *Angew Chem Int Ed Engl*, 43:2684-7 (2004).

Latroche et al., "Hydrogen storage in the giant-pore metal-organic frameworks MIL-100 and MIL-101", *Angew Chem Int Ed Engl*, 43: 8227-31 (2006).

Lee et al., "A robust porous material constructed of linear coordination polymer chains: reversible single-crystal to single-crystal transformations upon dehydration and rehydration", *Angew Chem Int Ed Engl*, 43:2798-801 (2004).

Lee et al., "Multifunctionality and crystal dynamics of a highly stable, porous metal-organic framework $[Zn_4O(NTB)_2]$", *J Am Chem Soc*, 127:6374-81 (2005).

Liu et al., "Assembly of metal-organic frameworks (MOFs) based on indium-trimer building blocks: a porous MOF with soc topology and high hydrogen storage", *Angew Chem Int Ed Engl*, 46:3278-83 (2007).

Min et al., "Silver(I)-polynitrile network solids for anion exchange: anion-induced transformation of supramolecular structure in the crystalline state", *J Am Chem Soc*, 122:6834-40 (2000).

Mulfort et al., "Chemical reduction of metal-organic framework materials as a method to enhance gas uptake and binding", *J Am Chem Soc*, 129:9604-5 (2007).

Oh et al., "Chemically tailorable colloidal particles from infinite coordination polymers", *Nature*, 438:651-4 (2005).

Pan et al., "Zn(tbip) ($H_2$tbip=5-tert-butyl isophthalic acid): a highly stable guest-free microporous metal organic framework with unique gas separation capability", *J Am Chem Soc*, 128:4180-1 (2006).

Panella et al., "Hydrogen physisorption in metal-organic porous crystals", *Adv Mater*, 17:538-41 (2005).

Pangborn et al., "Safe and convenient procedure for solvent purification", *Organometallics*, 15:1518-20 (1996).

Welch et al., "Synthesis and ligand-exchange kinetics of the solvated trigonal-prismatic clusters $[W_6CCl_{12}L_6]2+$(L=dmf, py)", *Angew Chem Int Ed Engl*, 46:3494-6 (2007).

Wu et al., "A homochiral porous metal-organic framework for highly enantioselective heterogeneous asymmetric catalysis", *J Am Chem Soc*, 127:8940-1 (2005).

Zhao et al., "Coordination polymers containing 1D channels as selective luminescent probes", *J Am Chem Soc*, 126:15394-5 (2004).

* cited by examiner

METAL-ORGANIC FRAMEWORK MATERIALS BASED ON ICOSAHEDRAL BORANES AND CARBORANES

CROSS-REFERENCE TO RELATED APPLICATIONS

This application claims the benefit of U.S. provisional application No. 60/962,195, filed Jul. 27, 2007, which is incorporated herein by reference in its entirety.

STATEMENT OF GOVERNMENTAL SUPPORT

This invention was made with government support under US Dept. of Energy Grant No. DE-FG02-01ER15244; and Army Research Office Grant No. W911NF-06-0116. The government has certain rights in this invention.

BACKGROUND

Tailorable inorganic coordination polymers, in particular, metal-organic frameworks (MOFs) comprise an important emerging class of materials. See Oh, et al *Nature* 438:651-654 (2005); Min, et al. *J. Am. Chem. Soc.* 122:6834-6840 (2000); Cho, et al. *Chem. Commun.* 2563-2565 (2006); Wu, et al. *J. Am. Chem. Soc.* 127:8940-8941 (2005); Gomez-Lor, et al. *Chem. Mater.* 17:2568-2573 (2005); Kitaura, et al. *Angew. Chem., Int. Ed.* 43:2684-2687 (2004); Evans, et al. *Chem. Mater.* 13:2705-2712 (2001); Lee, et al. *J. Am. Chem. Soc.* 127:6374-6381 (2005); Dinca, et al. *J. Am. Chem. Soc.* 127: 9376-9377 (2005); Zhao, et al. *J. Am. Chem. Soc.* 126:15394-15395 (2005); Liu, et al. *Angew. Chem. Int. Ed.* 46:3278-3283 (2007); Chen, et al. *Angew. Chem. Int. Ed.* 44:4745-4749 (2005); Dinca, et al. *J. Am. Chem. Soc.* 128:16876-16883 (2006); Choi, et al. *J. Am. Chem. Soc.* 126:15844-15851 (2004); Lee, et al. *Angew. Chem., Int. Ed.* 43:2798-2801 (2004); Bradshaw, et al. *Acc. Chem. Res.* 38:273-282 (2005); Kitagawa, et al. *Angew. Chem., Int. Ed.* 43:2334-2375 (2004); Latroche, et al. *Angew. Chem., Int. Ed.* 45:8227-8231 (2006); Welch, et al. *Angew. Chem., Int. Ed.* 46:3494-3496 (2007); and Mulfort, et al. *J. Am. Chem. Soc.* 129:9604-9605 (2007). MOFs are noteworthy for their structural and chemical diversity, high internal surface areas and often permanent microporosity. As such, MOFs have attracted great interest for numerous applications including ion exchange, heterogeneous catalysis, optoelectronics, gas separation, gas sensing, and gas storage, in particular $H_2$ storage. Among the factors useful for attaining high gravimetric uptake of $H_2$ are small pores, open metal coordination sites, and low framework mass. To date, no metallic, carborane-based frameworks have been made. Organic, metal-free, high porosity covalent organic frameworks have been reported. See El-Kaderi, et al. *Science,* 316:268-272 (2007). Thus, a need exists for metal organic frameworks, which can be used in gas storage and other applications.

SUMMARY

The present invention provides MOFs, which are polymeric crystalline structures of metals and boron rich ligands, such as carborane (CB) ligands or icosahedral boranes. These MOFs can have gas uptake properties. The CB ligand can be one as depicted in Scheme 1, 2, or 3, below. The metal can be any metal capable of coordinating to a boron rich ligand. The MOF can have solvent molecules coordinated to the metal centers or can be substantially free of solvent. In one embodiment, MOFs are polymeric crystalline structures of $Zn_3(OH)$ (p-CDC)$_{2.5}$L$_m$, wherein p-CDC is the CB ligand 1,12-dihydroxycarbonyl-1,12-dicarba-closo-dodecaborane, L is a solvent, and m is an integer from 0 to 4. In some embodiments, L is diethylformamide (DEF) or dimethylformamide (DMF). In some cases, m is 2 or 4. In various embodiments, the pore size of the MOFs disclosed herein are about 4 Å to about 11 Å, and in specific embodiments, are about 4.5 Å to about 9.5 Å. In various embodiments, the gas uptake of the MOFs disclosed herein is about 0.5 wt % to about 2.4 wt %, or about 1.3 wt % to about 2.1 wt %, at 77 K and 1 atm.

In another aspect, disclosed herein are compositions of the MOFs and further comprising a binder, organic viscosity-enhancing compound, liquid, or combination thereof. In some embodiments, the binder is silica, an oxide of magnesium or beryllium, a clay, or mixtures thereof. In various embodiments, the organic viscosity-enhancing compound is cellulose, starch, polyacrylate, polymethacrylate, polyvinyl alcohol, polyvinylpyrrolidone, polyisobutene, polytetrahydrofuran, or mixtures thereof. In some cases, the liquid is water, methanol, ethanol, propanol, n-butanol, isobutanol, tert-butanol, or mixtures thereof.

In yet another aspect, disclosed herein are methods of storing a gas using the MOFs or compositions, comprising exposing the MOF or composition to a gas of interest under conditions sufficient for the MOF to uptake the gas. Typically, the conditions sufficient include temperature (less than about 150 K, and preferably less than 100 K) and pressure (about 0.1 atm to about 3 atm, and preferably about 0.5 atm to about 1.5 atm). In some specific cases, the gas is hydrogen.

DETAILED DESCRIPTION

Figure 1:
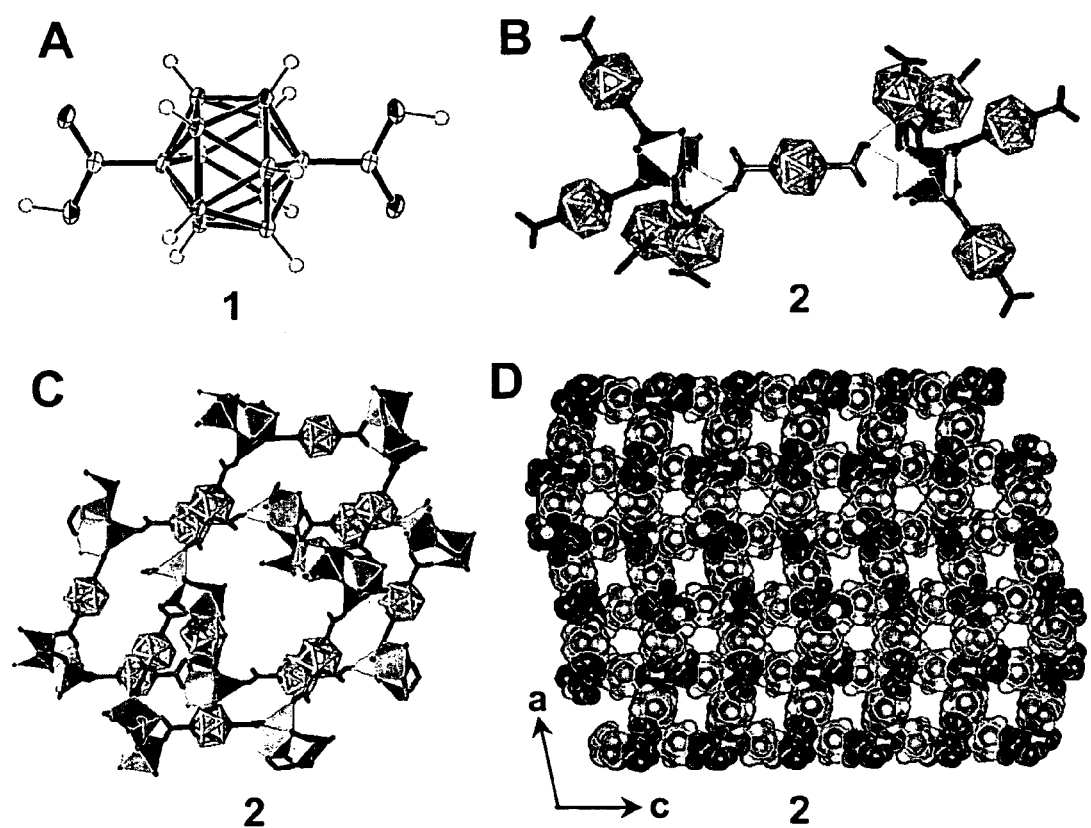
FIG. 1 shows a crystallographically derived (A) structure of 1, the CB ligand p-CDC, a carborane building block of the MOFs disclosed herein; (B) topology and connectivity of 2, a MOF of 1; (C) three dimensional topology and connectivity of 2; and (D) space-filling packing diagrams of 2 down b axes with DEF removed from $Zn_3OH$ clusters, and coordinated DEF molecules are omitted from (B)-(D) for clarity.

Disclosed herein are MOFs, which are polymeric crystalline structures of boron rich ligands, such as carboranes (CB) or icosahedral boranes, methods of synthesizing these MOFs, and methods of using these MOFs in gas storage. The MOFs disclosed herein are stable to air and water. Without being bound by theory, it is postulated that this stability is due to the rigidity of the boron rich ligands and the inability for $\pi$-$\pi$ stacking, as compared to previously reported MOFs.

As used herein, the term "polymeric crystalline structures" refers to polymers of monomers which are metals coordinated to boron rich ligands. The materials produced herein are "crystalline" which refers to the ordered definite crystalline structure of the material which is unique and thus identifiable by a characteristic X-ray diffraction pattern.

Carboranes are icosahedral carbon-containing boron clusters possessing several material-favorable properties including rigidity, thermal stability, and chemical stability. Dicarbon carboranes of the form $C_xB_{x-2}H_x$ ($6 \leq x \leq 12$) may be regarded as three-dimensional delocalized aromatic systems in which surface bonding and core bonding correspond to σ-bonding and π-bonding, respectively. See, Hawthorne, *Advances in Boron Chemistry*, Special Publication No. 201, Royal Society of Chemistry, London, 82:261 (1997). These compounds can be prepared on the kilogram scale and have been used for a variety of applications, including boron neutron capture therapy, molecular delivery devices in biomedicine and molecular motors.

The MOFs disclosed herein are based upon metal coordination of the deprotonated form of boron rich ligands. Metals that can coordinate to boron rich ligands include transition and lanthanide metals. Specific examples of metals contemplated include, but are not limited to, any oxidation state of magnesium, calcium, strontium, barium, radium, aluminum, gallium, indium, thallium, silicon, germanium, tin, lead, arsenic, antimony, scandium, titanium, vanadium, chromium, manganese, iron, cobalt, nickel, copper, zinc, yttrium, zirconium, niobium, molybdenum, technetium, rubidium, rhodium, palladium, silver, cadmium, hafnium, tantalum, tungsten, rhenium, osmium, iridium, platinum, gold, mercury, lanthanum, cerium, praseodymium, neodymium, promethium, samarium, europium, gadolinium, terbium, dysprosium, holmium, erbium, thulium, and ytterbium. Specific metals and oxidation states contemplated for use in the MOFs disclosed herein include, but are not limited to, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, and $Bi^+$.

Dicarborane (CB) ligands include 1,12-dihydroxycarbonyl-1,12-dicarba-closo-dodecaborane (p-CDCH$_2$ (1); FIG. 1A) and carborane ligands as seen in Schemes 1, 2, and 3, below. Some of the ligands have been designated as B3CB, MCB2, BCPD, p-CDC, and p-bis-CDC. Some of the ligands of Scheme 3 comprise one or more CH groups. These CH groups can be transformed to be C(COOH) groups, allowing for coordination of metal ions via the carboxylate moiety.

p-CDC$^{2-}$ has approximately the same 2-D footprint as benzene-1,4-dicarboxylate (bdc), the strut defining the archetypal cubic framework compound, MOF-5 [$Zn_4O(bdc)_3$]$_n$. In comparison with other frameworks, MOF-5 is a good, albeit not spectacular, hydrogen storage material, at least at cryogenic temperatures (1.25 wt % at 77K and 1 atm). See Panella, et al. *Adv. Mater.* 17:538-541 (2005). By replacing benzene with the three-dimensional carborane (volume approximately that swept out by a rotating phenyl ring), a close structural analogue of MOF-5 can be obtained, but with smaller pores and therefore higher heats of adsorption. Such a change can lead to higher hydrogen loading at low temperatures and modest pressures and/or more persistent loading at higher temperatures. See Pan, et al. *J. Am. Chem. Soc.* 128:4180-4181 (2006).

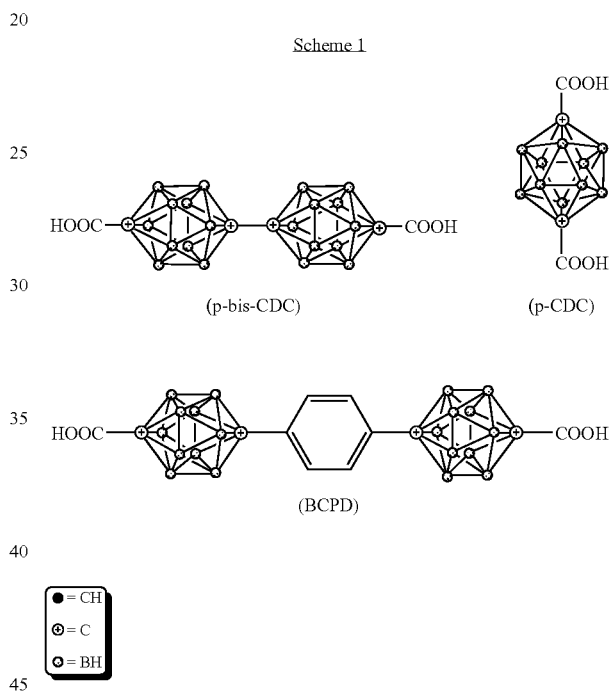

Scheme 1

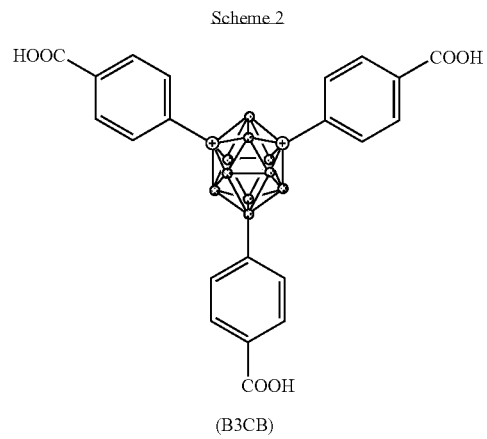

Scheme 2

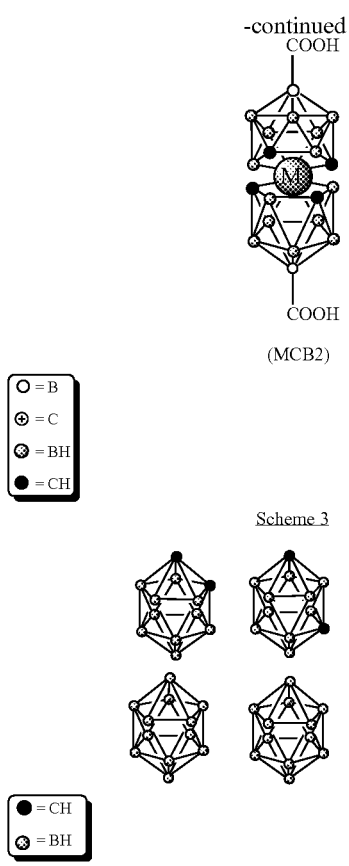

(MCB2)

○ = B
⊕ = C
⊗ = BH
● = CH

Scheme 3

● = CH
⊗ = BH

The CB ligands can then be coordinated with a metal to form MOFs. The MOFs can have other ligands incorporated into the polymeric structure, such as hydroxide (OH⁻) anions, or coordinated solvents. The number of coordinated solvents will depend upon the method of synthesizing the MOF. The longer the MOF is heated or the higher the temperature to which it is heated will result in fewer solvent molecules than for MOFs that were not heated or were heated at lower temperatures or for shorter periods of time. The solvent that is coordinated can be any solvent which is compatible with the synthesis of the monomeric metallic CB intermediates or during formation of the polymeric MOF itself. Non-limiting examples of such solvents include L can be any solvent compatible with the MOF material, or used during its synthesis. Some non-limiting examples of suitable solvents include diethylformamide (DEF), dimethylformamide (DMF), N-methylpyrrolidone (NMP), tetrahydrofuran, and pyridine.

The MOFs disclosed herein can be one dimensional (1D), two dimensional (2D), or three dimensional (3D). 1D MOFs are linearly aligned repeating units of the metal-ligand. 2D MOFs are repeating units of the metal-ligand arranged into sheet-like morphologies. The 3D MOFs are metal-ligand units arranged in a manner that is neither sheet-like nor linear. Regardless of the arrangement, the MOFs can then be arranged further into stacks or layers.

In some cases, the MOFs disclosed herein are substantially free of solvents. As used herein "substantially free" means that solvents are present in the MOF at levels less than 1 wt % by weight of the MOF, and preferably from 0 wt % to about 0.5 wt % by weight of the MOF. The solvent can be removed from the MOF by exposing the MOF to elevated temperatures under reduced pressure, or by soaking the MOF in a low boiling solvent to exchange the coordinated solvent for the low boiling solvent, then exposing the MOF to reduced pressure. The amount of solvent in the MOF can be determined by elemental analysis or other known analytical techniques.

One class of MOFs disclosed are polymeric structures of repeating units of $Zn_3(OH)(p\text{-}CDC)_{2.5}L_m$, where L is a solvent molecule, as defined above, and m is an integer from 0 to 4. In preferred embodiments, L is DEF or DMF. M can be 0, 1, 2, 3, or 4.

The pore size of the MOFs as disclosed herein can be altered depending upon the number of solvent molecules coordinated or partially coordinated to the metal center. Typically, the pore size of the MOF will be about 4.5 Å to about 11 Å, but can be about 4.5 Å to about 9.5 Å. In preferred embodiments, the most prevalent pore size of the MOF is about 4.5 Å to about 5.5 Å. In some preferred embodiments, more than 50%, more than 60%, more than 70%, more than 80%, or more than 90% of the pore sizes of the MOF are 10 Å or less.

The Brunauer, Emmett, and Teller (BET) surface area of the MOFs disclosed herein can be about 100 to about 4000 $m^2/g$. In some cases, the BET surface area about 100 to about 2500 $m^2/g$, about 150 to about 2000 $m^2/g$, about 150 to about 1500 $m^2/g$, about 150 to about 1000 $m^2/g$, and about 100 to about 250 $m^2/g$.

Initial synthesis of MOFs as disclosed herein typically result in a number of fully or partially coordinated solvent molecules, e.g., a MOF designated 2. Upon exposure to elevated temperatures (e.g., 100° C. or higher) and decreased pressures, at least a portion of the solvent molecules are de-coordinated, providing MOF structures that have excellent adsorption properties. The removal of at least some of the coordinated solvent ligands provides for increase gas uptake. For example, upon exposure to 100° C. under vacuum, a MOF as disclosed herein, designated 3, has a gas uptake of about 0.7 wt % at 77K and 1 atm, whereas the same material, when exposed to 300° C. under vacuum, provides a MOF designated 4 that exhibits a gas uptake of about 2.1 wt % at 77 K and 1 atm. The MOFs disclosed herein typically have a gas uptake of about 0.5 wt % to about 2.4 wt % at 77K and 1 atm. In some specific examples, the gas uptake of the MOF is about 0.7 wt % to about 2.2 wt %, about 1.0 wt % to about 2.1 wt %, or about 1.3 wt % to about 2.1 wt %.

Figure 11:
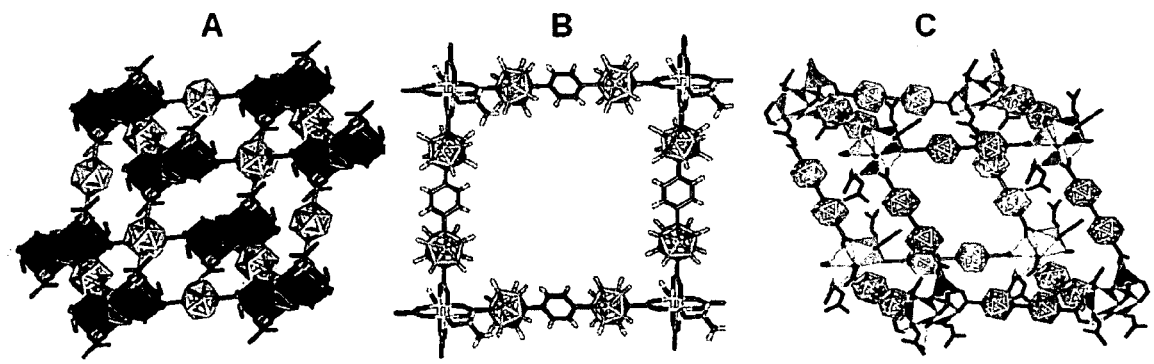
FIG. 11A shows a crystal structure of a MOF of $Co_4(OH)_2$(p-CDC)$_3$(DMF)$_2$.
FIG. 11B shows a crystal structure of a MOF of $Zn_2$(p-BCPD)$_2$(ethanol)($H_2O$).
FIG. 11C shows a crystal structure of a MOF of $Zn_3(OH)$(p-bis-CDC)$_{2.5}$(DMF)$_4$.
Figure 12:
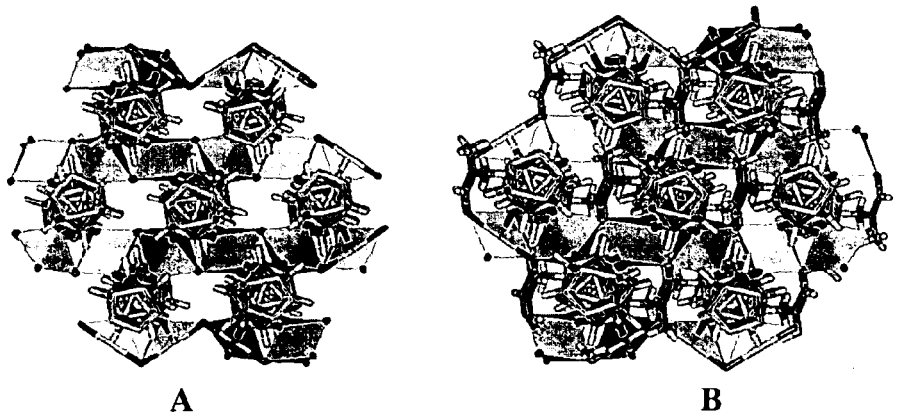
FIG. 12A shows a crystal structure of a MOF of MnCDC (DMF) and FIG. 12B is the crystal structure with the solvents coordinated.

Crystal structures of some contemplated MOFs are seen in FIG. 11. FIG. 11A shows the crystal structure of a MOF of Co and Another aspect are compositions comprising the MOFs as disclosed herein. The compositions can include one or more MOF as disclosed herein and a binder, an organic viscosity-enhancing compound, and/or a liquid for converting the MOF into a paste. The composition can then be used as a means of storing gas, by exposing the composition to a gas and allowing the MOF of the composition to uptake the gas.

A number of inorganic compounds can be used as binders. Non-limiting examples include titanium dioxide, hydrated titanium dioxide, hydrated alumina or other aluminum-containing binders, mixtures of silicon and aluminum compounds, silicon compounds, clay minerals, alkoxysilanes, and amphiphilic substances. Other binders are in principle all compounds used to date for the purpose of achieving adhesion in powdery materials. Compounds, in particular oxides, of silicon, of aluminum, of boron, of phosphorus, of zirconium and/or of titanium are preferably used. Of particular interest as a binder is silica, where the $SiO_2$ may be introduced into the shaping step as a silica sol or in the form of tetraalkoxysilanes. Oxides of magnesium and of beryllium and clays, for example montmorillonites, kaolins, bentonites, halloysites, dickites, nacrites and anauxites, may furthermore be used as binders. Specific examples include tetramethoxysilane, tetraethoxysilane, tetrapropoxysilane and tetrabutoxysilane, the analogous tetraalkoxytitanium and tetraalkoxyzirconium compounds and trimethoxy-, triethoxy-, tripropoxy- and tributoxy-aluminum. The binder may have a concentration of from 0.1 to 20% by weight. Alternatively, no binder is used.

In addition, organic viscosity-enhancing substances and/or hydrophilic polymers, e.g. cellulose or polyacrylates can be used. The organic viscosity-enhancing substance used may likewise be any substance suitable for this purpose. Those preferred are organic, in particular hydrophilic polymers, e.g., cellulose, starch, polyacrylates, polymethacrylates, polyvinyl alcohol, polyvinylpyrrolidone, polyisobutene and polytetrahydrofuran.

There are no restrictions with regard to the optional liquid which may be used to create a paste-like composition of the MOFs disclosed herein. In addition to water, alcohols may be used. Accordingly, both monoalcohols of 1 to 4 carbon atoms and water-miscible polyhydric alcohols may be used. In particular, methanol, ethanol, propanol, n-butanol, isobutanol, tert-butanol and mixtures of two or more thereof are used.

Amines or amine-like compounds, for example tetraalkylammonium compounds or aminoalcohols, and carbonate-containing substances, such as calcium carbonate, may be used as further additives in the disclosed compositions. Such further additives are described in EP-A 0 389 041, EP-A 0 200 260 and WO 95/19222, which are incorporated fully by reference in the context of the present application.

Most, if not all, of the additive substances mentioned above may be removed from the composition by drying or heating, optionally in a protective atmosphere or under vacuum. In order to keep the MOF intact, the composition is preferably not exposed to temperatures exceeding 300° C. Heating/drying the composition under the mild conditions, in particular drying in vacuo, preferably well below 300° C. is sufficient to at least remove organic compounds out of the pores of the MOF. Generally, the conditions are adapted and chosen depending upon the additive substances used.

The order of addition of the components (optional solvent, binder, additives, MOF material) is not critical. It is possible either to add first the binder, then, for example, the MOF material and, if required, the additive and finally the mixture containing at least one alcohol and/or water or to interchange the order with respect to any of the aforementioned components.

Additional aspects and details of the disclosure will be apparent from the following examples, which are intended to be illustrative rather than limiting.

EXAMPLES

Starting materials were purchased from Sigma-Aldrich (ACS grade) and used without further purification unless otherwise noted. Diethyl ether ($Et_2O$) was purified by published methods (Armarego, et al., *Purification of Laboratory Chemicals*, Butterworth-Heinemann: Oxford, 1996; and Pangborn, et al., *Organometallics*, 15:1518 (1996)) and deoxygenated with nitrogen prior to use. Deuterated solvents were purchased and used as received from Cambridge Isotopes Laboratories. p-Carborane was provided by Professor M. F. Hawthorne.

Analytical thin layer chromatography (TLC) was performed using glass plates pre-coated with silica gel (0.25 mm, 60 Å pore size) with a fluorescent indicator (254 nm). Visualization was accomplished with UV light and/or palladium chloride ($PdCl_2$) in 6 M hydrochloric acid as a stain.

Powder X-ray diffraction (PXRD) patterns were recorded with a Rigaku XDS 2000 diffractometer using nickel-filtered Cu Kα radiation (λ=1.5418 Å). Thermogravimetric analyses (TGA) were performed on a Mettler-Toldeo TGA/SDTA851e. Absorption isotherms were measured with an Autosorb 1-MP from Quantachrome Instruments. Infrared spectra (FTIR) were obtained on a BIO RAD FTS-60 spectrophotometer. Elemental analysis was performed by Atlantic Microlab, INC. (Norcross, Ga.). $^1H$ NMR and $^{13}C$ NMR were done on a Varian Inova 500 spectrometer at 500 MHz and 125 MHz, respectively. $^{11}B$ NMR was done on a Varian Inova 400 spectrometer at 128.5 MHz. NMR splitting patterns are designated as singlet (s), doublet (d), triplet (t), quartet (q). Splitting patterns that could not be interpreted or easily visualized are designated multiplet (m) or broad (br). Coupling constants are reported in Hertz (Hz).

Example 1

Preparation of 1,12-Dihydroxycarbonyl-1,12-dicarba-closo-dodecaborane (1, p-CDC)

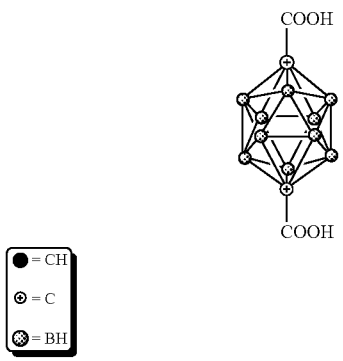

Butyl lithium (1.6 M, 35 mL, 56 mmoles) was added via syringe to 2 grams (13.9 moles) of 1,12-dicarba-closo-dodecacarborane (p-carborane) dissolved in 150 mL of dry diethyl ether at 0° C. The reaction mixture was warmed to room temperature and refluxed for 1.5 hours. The reaction was then cooled to −78° C. using a dry ice/acetone bath. Carbon dioxide was bubbled into the reaction mixture for an hour while stirring. The reaction mixture was concentrated, and 3 M hydrochloric acid (100 mL) was added to the resulting white solid. The precipitate was filtered and washed with chilled water, hexanes, then chloroform. The product 1 was obtained as a white solid (2.81 g, 87% yield) and dried in vacuo overnight. Single crystals of 1 were grown from ethanol:water (1:1) by slow evaporation over several days. $^1H$ NMR ($d_8$-THF, 500 MHz): δ 11.69 (bs, 2H, COOH), 3.2-1.6 (m, 10H, BH); $^{13}C$ NMR ($d_8$-THF, 125 MHz): δ 162.5 (s, COOH), 162.5 (s, BC); $^{11}B\{^1H\}$ NMR ($CDCl_3$): δ −13.9.

Preparation of $[Zn_3(OH)(p\text{-}CDC)_{2.5}(DEF)_4]_n$ (2)

A small scale amount of $[Zn_3(OH)(p\text{-}CDC)_{2.5}(DEF)_4]_n$ (2) was prepared as follows. Exact amounts of $Zn(NO_3).6H_2O$ (33 mg, 0.11 mmole) and 1,12-dicarboxylic-1,12-dicarba-closo-dodecaborane (8.3 mg, 0.035 mmole) were dissolved in 1 mL dimethylformamide (DMF). The solution was heated at 80° C. for 24 hours. Larger scale amounts were prepared as follows. Exact amounts of $Zn(NO_3).6H_2O$ (1.20 g, 4.03 mmole) and 1,12-dicarboxylic-1,12-dicarba-closo-dodecaborane (0.30 g, 1.28 mmole) were dissolved in 36 mL 1:1

DMF:ethanol. The solution was heated at 80° C. for 24 hours. The crystals were collected by filtration, washed with DMF and ethanol, and dried in air, providing 480 mg 2 (32% yield based on zinc). The crystals of 2 were also heated at 100° C. in vacuo to provide 3.

Preparation of DEF-Free MOF Based Upon 2 (4)

Crystals of 2 were heated in vacuo at 300° C. for 24 hours to produce 4. Anal. Calcd. for $Zn_3B_{25}C_{10}H_{30}O_{13}$ (4.$H_2O$)C, 14.3; H, 3.6; N, 0.0. Found: C, 13.95; H, 3.47; N, 0.0.

Analysis of Properties of 3 and 4

Figure 4:
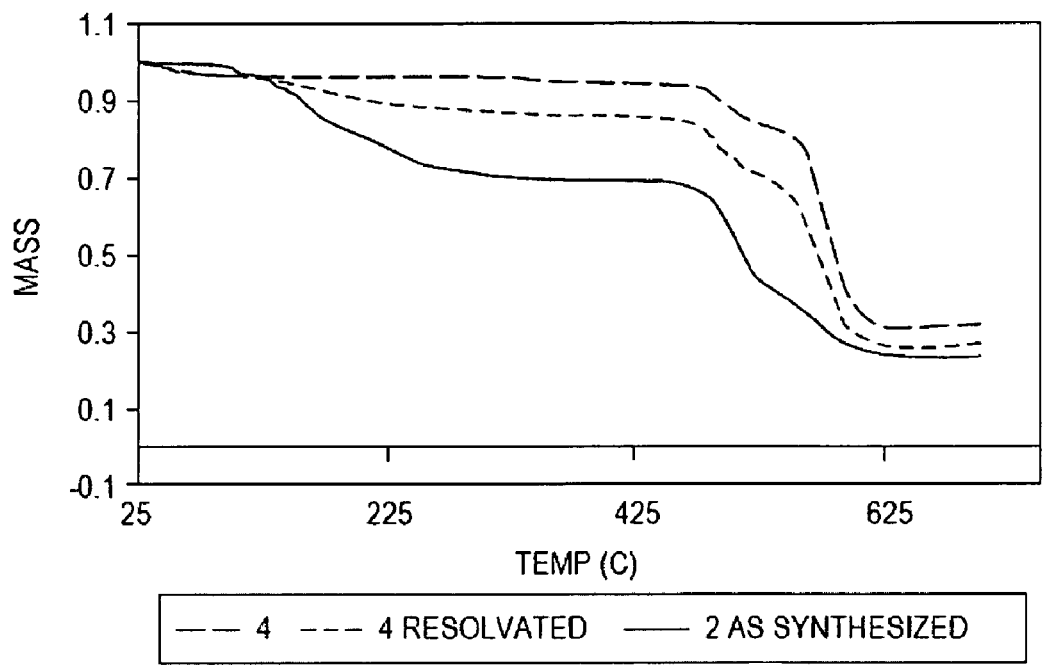
FIG. 4 shows TGA analysis of 2, 4, and 4 resolvated.

The solvathermal synthesis disclosed herein yielded a complex MOF of the formula $[Zn_3(OH)(p\text{-}CDC)_{2.5}(DEF)_4]_n$ (2) [DEF=diethylformamide] (FIG. 1). X-ray analysis of a single crystal of 2 revealed a structure in which two of the three zinc ions are coordinated to two DEF molecules each in an octahedral geometry. In addition, one of the dicarboxylate ligands in the structure is ligated to zinc through only one oxygen atom. The zincs are further connected by a triply bridging hydroxide ion. Thermogravimetric analysis (TGA) of 2 revealed mass losses between 125-175° C. and 175-250° C., assigned to free and coordinated DEF respectively, but no further mass loss up to 500° C. (See FIG. 4.) Elemental analysis measurements of the crystalline material heated under vacuum at 300° C. confirmed the removal of the coordinated DEF. Powder x-ray diffraction (PXRD) measurements established that although the crystallinity is retained, the structure is irreversibly altered. Although a single-crystal structure of the DEF-free version of the MOF (4) has yet to be isolated (FIG. 2A), infrared data strongly suggest that the partially coordinated carboxylate of 2 becomes fully coordinated in 4 (see FIG. 5). Nonetheless, the number of coordination sites occupied by DEF in 2 is greater than the number of coordination sites needed for complete coordination of p-$CDC^{2-}$. This mismatch may result in coordinatively unsaturated or at least highly reactive metal sites.

Figure 6:
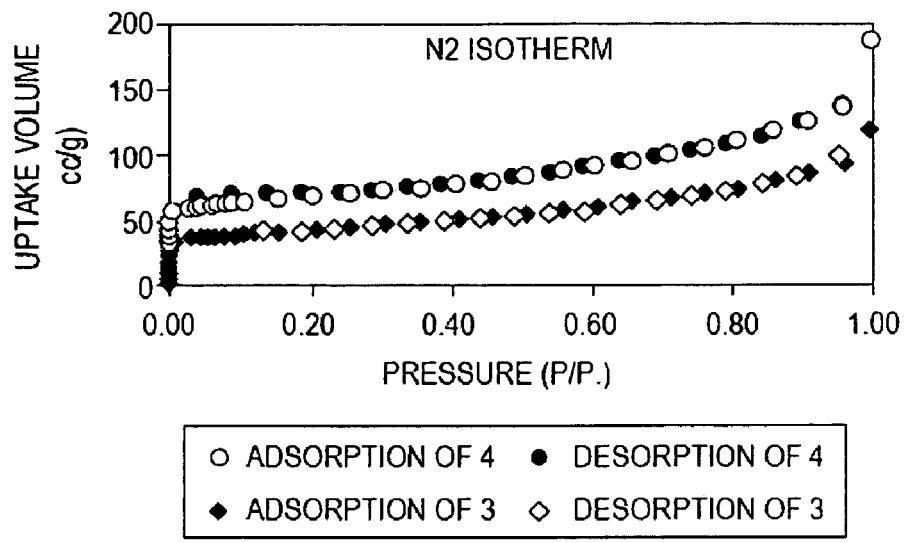
FIG. 6 shows adsorption (empty squares) and desorption (filled squares) of 4 (top) and adsorption (filled squares) and desorption (empty squares) of 3 (bottom) of $N_2$ at 77 K.
Figure 7:
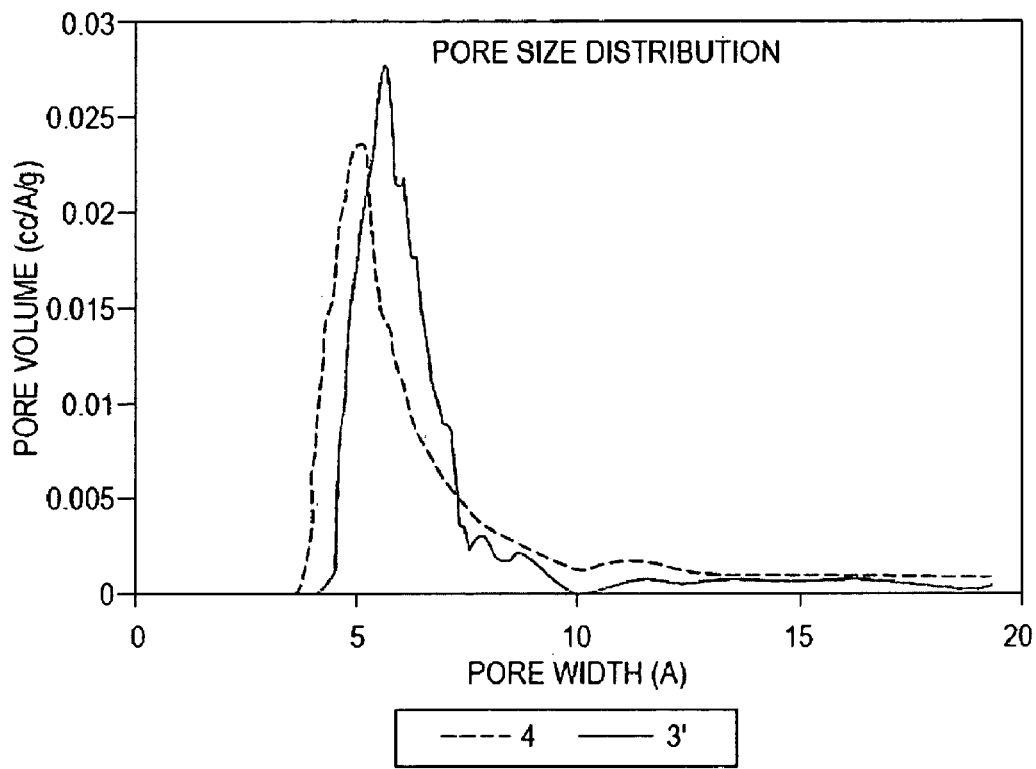
FIG. 7 shows pore size distribution of 3 and 4.

Adsorption measurements (FIG. 6) were used to determine the $N_2$-accessible surface areas of 3 (compound 2 evacuated at 100° C.) and 4. The Brunauer, Emmett, and Teller (BET) surface areas are 248 and 152 $m^2/g$, respectively. Notably, despite the removal of coordinated DEF, the conversion of 3 to 4 decreases the size of the most prevalent pores from 6 to 5 Å (FIG. 7).

Figure 3:
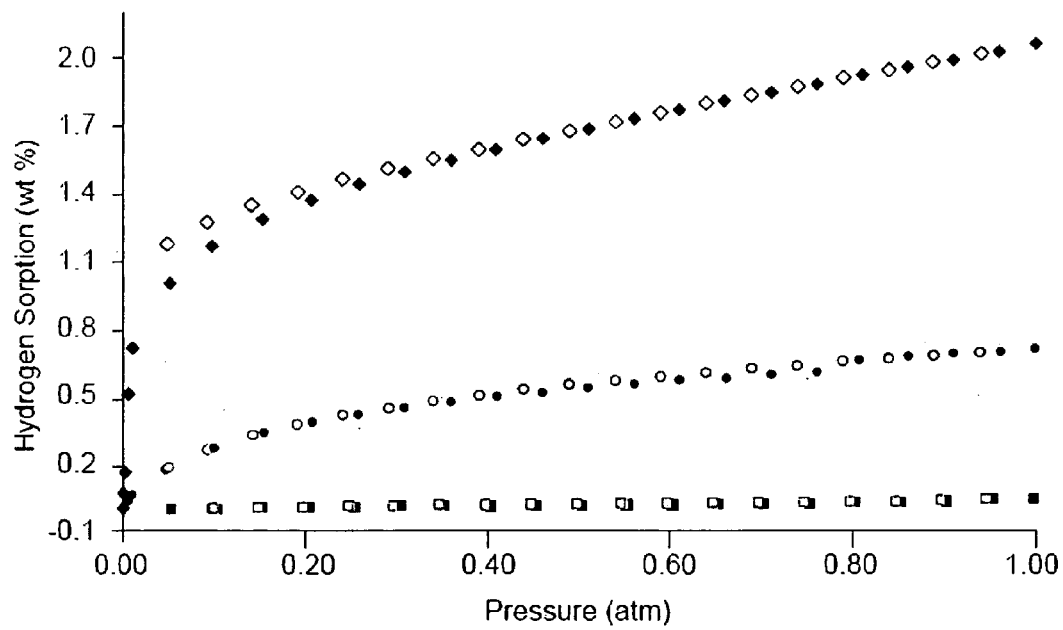
FIG. 3 shows the adsorption (solid squares) and desorption (empty squares) isotherms for $H_2$ uptake by (bottom) chloroform treated 2; (middle) 3; and (top) 4, all at 77 K.

In contrast to the modest $N_2$ adsorption, 4 has high $H_2$ uptake at 77K: 2.1% at 1 atm. This uptake is triple the uptake of 3 (volumetric measurements; FIG. 3) and stands in striking contrast to unheated samples of 2, which showed no uptake even after one week of exposure to chloroform, a solvent which is often effective for solvent exchange, and ambient vacuum. Further comparison of 3 and 4 revealed that at 1 atm the latter takes up about 6 additional $H_2$ molecules per [$Zn_3$(OH)]$_7$— cluster. Without intending to be bound by theory, the enhanced uptake may be attributable to putative open metal sites, and/or the reduction of pore size may also play a role. The $H_2$ results for 4 compare favorably to those for a variety of other MOFs measured under the same conditions and indeed are exceeded by only three other framework materials (See Liu, et al. *Angew. Chem. Int. Ed.* 46:3278-3283 (2007); Chen, et al. *Angew. Chem. Int. Ed.* 44:4745-4749 (2005); and Dinca, et al. *J. Am. Chem. Soc.* 128:16876-16883 (2006)), where the highest uptake reported was 2.45%.

Figure 2:
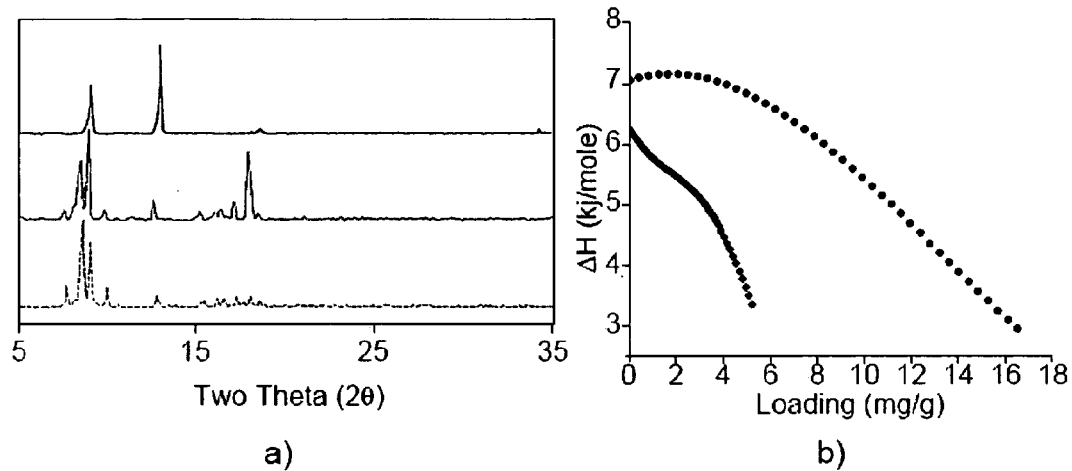
FIG. 2A shows PXRD patterns for (bottom) a simulated single-crystal structure of 2, (middle) 2 as synthesized, and (top) 4, as synthesized from 2 (heated to 300° C.).
FIG. 2B shows the heats of adsorption ($\Delta H_{ads}$) for $H_2$ in 4 (right) and 3 (left), where 3 is derived from 2 (heated to 100° C.).

Isosteric heats of adsorption for $H_2$ in 3 and 4 were obtained by fitting 77 and 87K isotherms to appropriate virial equations (FIG. 2B). See Czepirski, et al. *Chem. Eng. Sci.* 44:797-801 (1989). $\Delta H_{ads}(H_2)$ values for 4 are substantially higher than for 3 over the entire loading range. These results are likewise qualitatively consistent with effects expected from reduction of pore size and/or formation of open metal coordination sites.

The first carborane-based MOF (2) has been synthesized. Removal of the coordinated solvent molecules triples the uptake of $H_2$ by the material at 77K and 1 atm (4 vs. 3) despite a decrease in surface area and reduction of $N_2$-accessible pore volume. The resistance to pore collapse upon conversion of 3 to 4 likely reflects the rigidity of the dicarborane, its 3-dimensional sterics, and its inability to benefit greatly from stacking-type (collapsed structure) van der Waals interactions.

Single crystals were mounted on a Bruker SMART CCD 1000 diffractometer equipped with a graphite-monochromated MoKα (λ=0.71073 Å) radiation source in a cold nitrogen stream. All crystallographic data were corrected for Lorentz and polarization effects (SAINT), and face-index absorption. The structures were solved by direct methods and refined by the full-matrix least squares method on $F^2$ with appropriate software implemented in the SHELXTL program package. In the structure of 2, three of the four coordinated DEF molecules could be reasonably modeled. Remaining contributions from disordered DEF coordinated to the node and within the pores were removed by the SQUEEZE routine (PLATON). All the non-hydrogen atoms were refined anisotropically. Hydrogen atoms on the carborane cage in 2 and 1 were found in the difference map and hydrogen atoms on the solvent molecules were added at their geometrically ideal positions. One ethanol molecule is reasonably modeled in 1.

| Crystal Data and Structure Refinement for 1 and 2 | | |
|---|---|---|
| | Compound | |
| | 1 | 2 |
| Empirical formula | $C_4H_{12}B_{10}O_4$ | $C_{25}H_{59}B_{25}N_3O_{15}Zn_3$ |
| Formula weight | 232.24 | 1108.11 |
| Crystal color, habit | Colorless, plate | Colorless, plate |
| Crystal dimension (mm$^3$) | 0.170 × 0.123 × 0.045 | 0.350 × 0.284 × 0.063 |
| Crystal system | triclinic | orthorhombic |
| Space group | P-1 | Pbcn |
| a (Å) | 6.6388(10) | 39.356(5) |
| b (Å) | 7.1089(11) | 14.5154(18) |
| c (Å) | 7.1799(11) | 21.629(3) |
| α (deg) | 78.937(2) | 90 |
| β (deg) | 74.844(2) | 90 |
| γ (deg) | 62.838(2) | 90 |
| V (Å$^3$) | 289.96(8) | 12356(3) |
| Z | 1 | 8 |
| ρ (calcd, g/cm$^3$) | 1.330 | 1.191 |
| μ (cm$^{-1}$) | 0.086 | 1.205 |
| Goodness-of-fit on $F^2$ | 1.079 | 1.048 |
| R | 0.0523 | 0.0655 |
| $R_W$ | 0.1398 | 0.1807 |

Absorption Measurements

Samples of known weight were evacuated under $10^{-5}$ torr dynamic vacuum for 24 hours on an Autosorb 1-MP from Quantachrome Instruments prior to gas absorption measurements. The evacuated sample was weighed again to obtain the sample weight.

Isosteric Heat of Absorption

Figure 8:
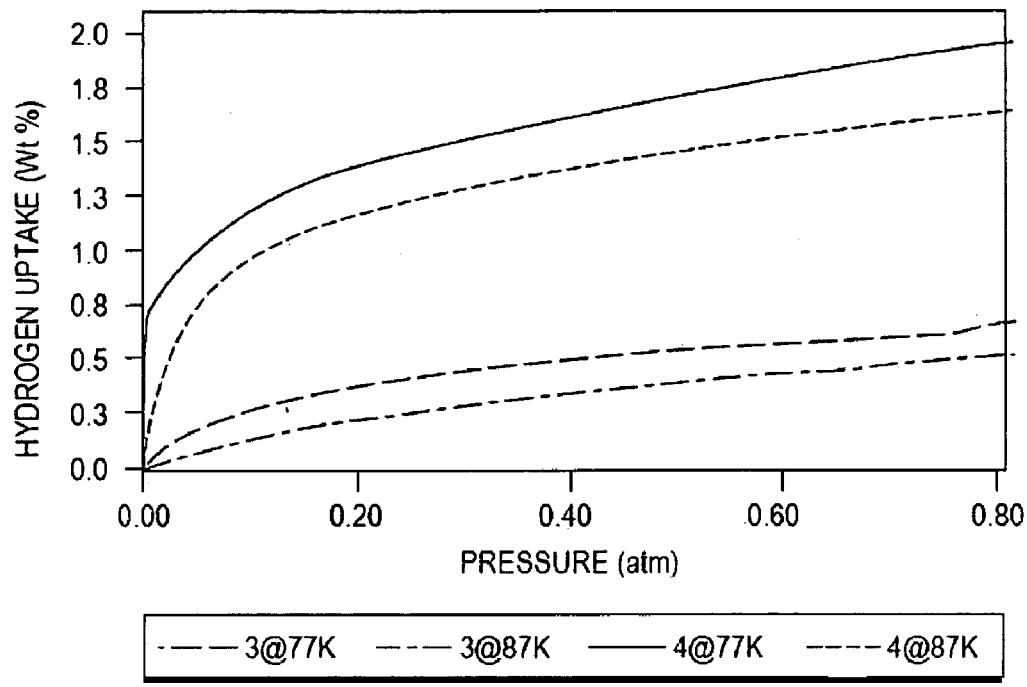
FIG. 8 shows the $H_2$ isotherms of 3 at 87 K (bottom—first line) and 77 K (second line) and of 4 at 87 K (third line) and 77 K (top—fourth line).
Figure 9:
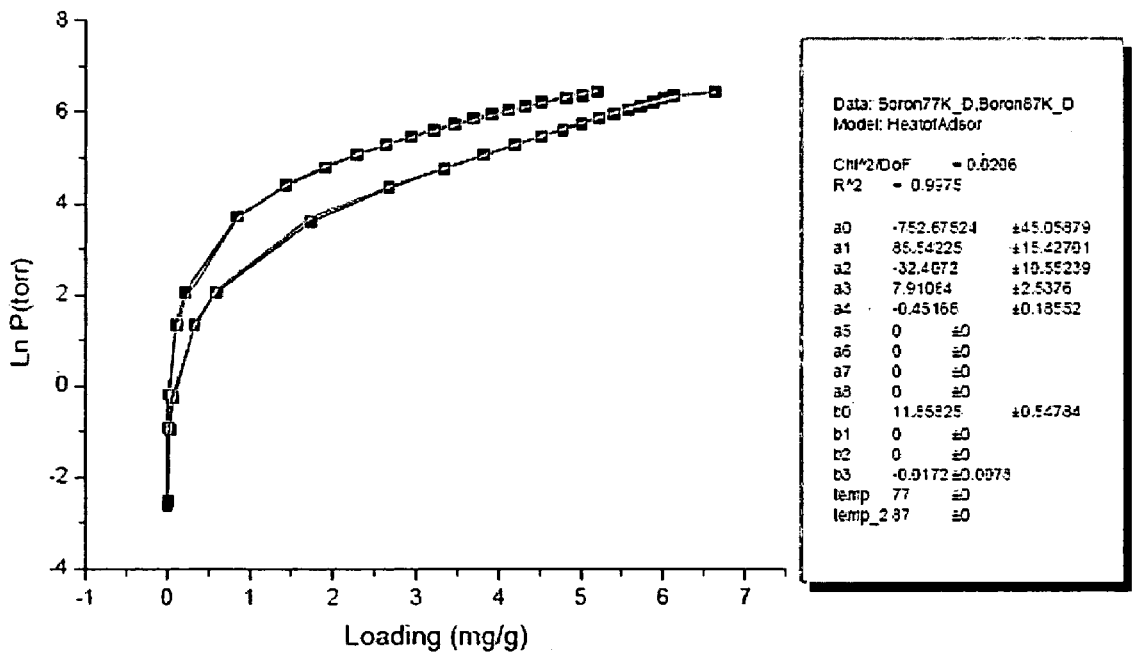
FIG. 9 shows the $H_2$ isotherm of 3 at 77 K and 87 K (filled squares) and the virial equation fit of the same.
Figure 10:
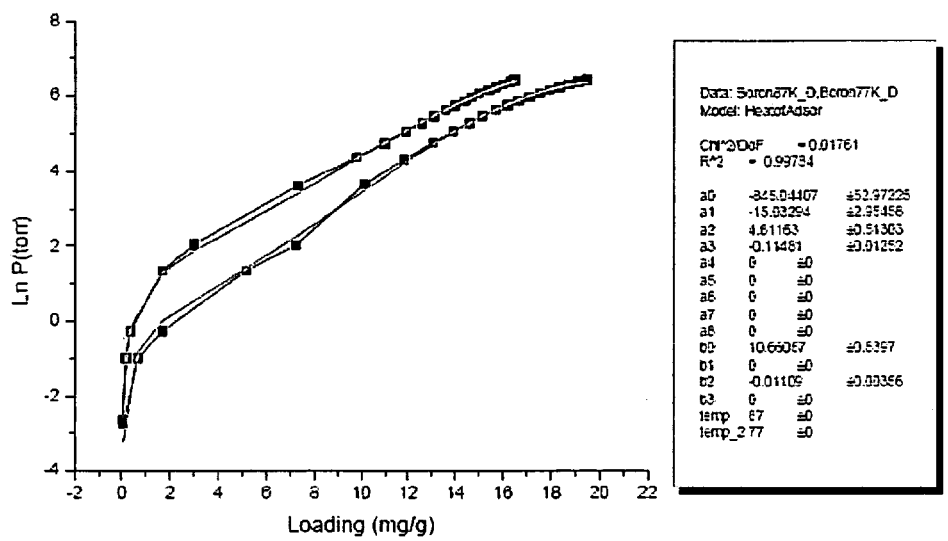
FIG. 10 shows the $H_2$ isotherms of 4 at 77 K and 87 K (filled squares) and the virial equation fit of the same.

The hydrogen isotherms obtained at 77 K and 87 K (FIG. 8) were fit to the following virial equation (Czepirski, et al., *J Chem Eng Sci*, 44:787 (1989)):

$$\ln p = \ln N + \frac{1}{T}\sum_{i=0}^{m} a_i N^i + \sum_{i=0}^{n} b_i N^i$$

and the resulting heat of absorption is shown in FIG. 9 (for 3) and FIG. 10 (for 4).

The heats of adsorption of 3 and 4 were calculated from the fitting parameters in the following equation:

$$q_{st}(N) = -R\sum_{i=0}^{m} a_i N^i$$

Figure 5:
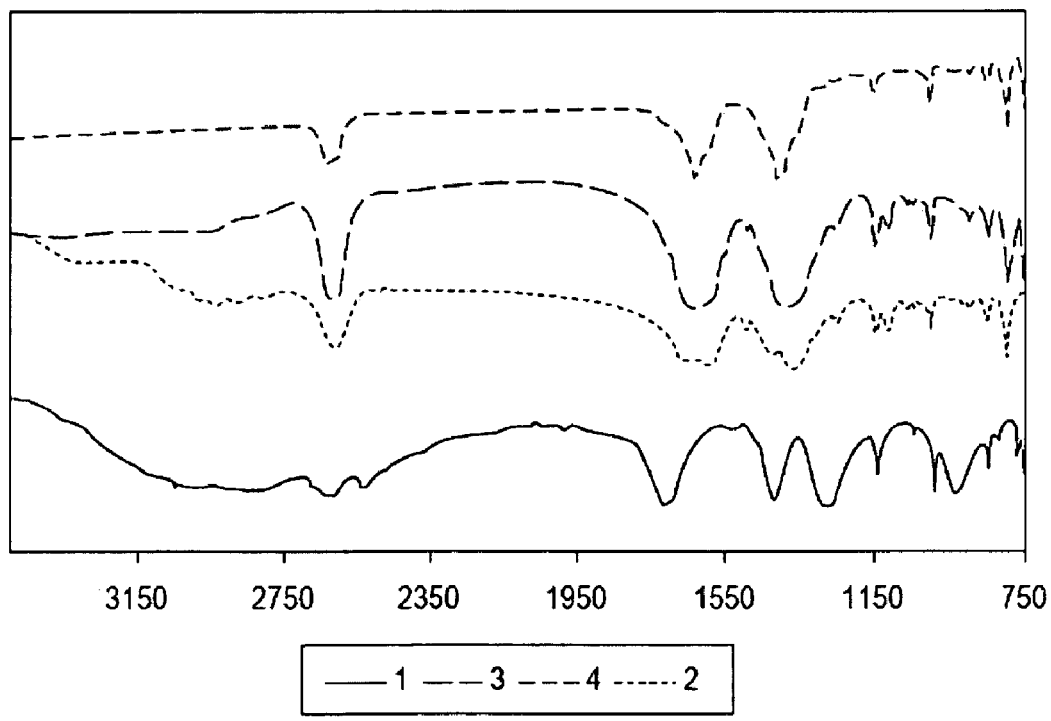
FIG. 5 shows Fourier-transform infrared spectra (FTIR) of 1 (bottom—first spectrum), 2 (second spectrum), 3 (third spectrum), and 4 (top—fourth spectrum).

The FTIR spectra of 1, 2, 3, and 4 are shown in FIG. 5. The peaks for v(CO) at about 1410 and 1640 cm$^{-1}$ transition to a sharper set of peaks when the free and coordinated solvent molecules are removed (see spectrum for 4). Elemental analysis indicates the complete removal of DEF (or DMF) solvent molecules. In structure 4 v(CO) peaks become significantly sharper compared to structure 3, which indicates complete coordination of the ligands of 4. The peaks in 4 are consistent with the presence of mainly fully coordinated carboxylates. There is also a small peak near 1700 cm$^{-1}$ that may correspond to a stretch for a non-coordinated C=O (see spectrum for 1). The crystal structure of 2 shows a ratio of one partially coordinated COO$^-$ unit to five fully coordinated COO$^-$ units.

Example 2

Preparation of Other Carborane Ligands

Other carborane ligands for use in MOFs as disclosed herein can be prepared from p-carborane, as outlined in the following scheme.

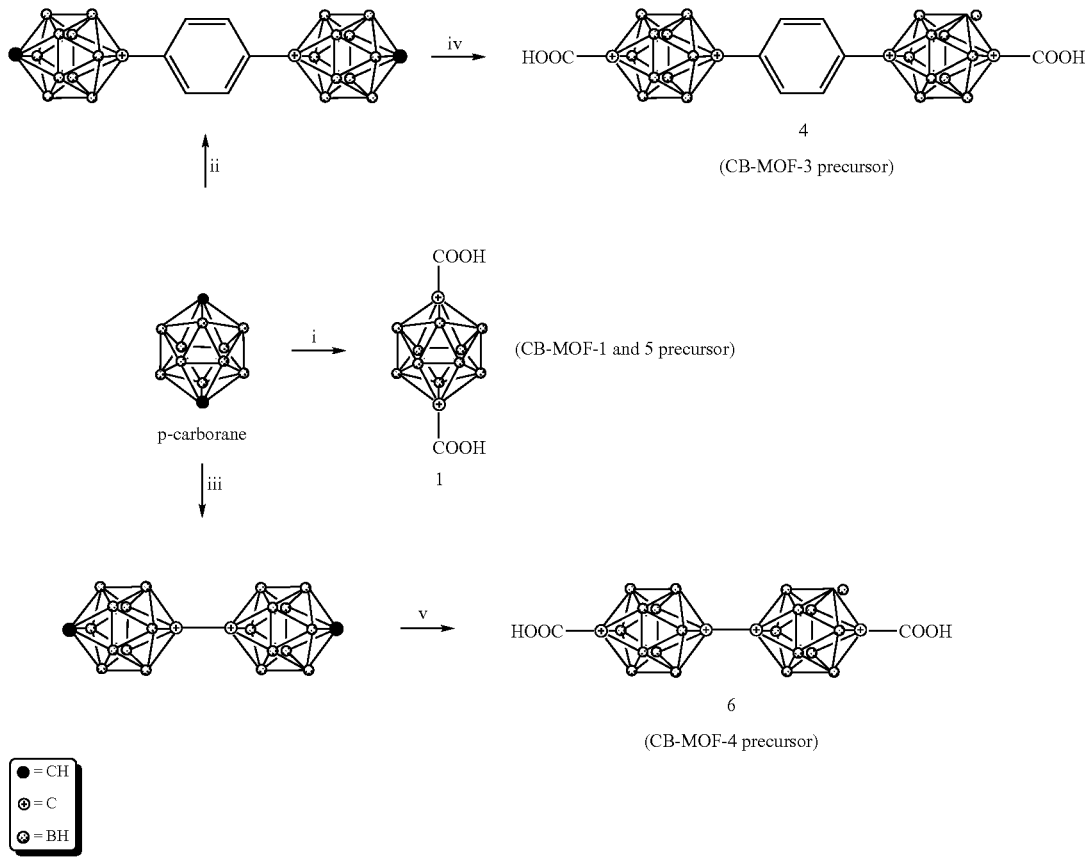

Synthesis of the carborane ligand precursors as seen in Scheme 1, p-bis-CDC 6, p-CDC 1, and BSPD 4, were as follows. For step (i) conditions: mixture of carborane and butyl lithium in ether and exposure to CO$_2$, cooled from 0° C. to −80° C. The yield of p-CDC was 80%. For step (ii) p-carborane, 1,4-iodobenzene, and butyl lithium were reacted in ether and warmed from 0° C. to room temperature. Then copper (I) chloride in pyridine was added and the mixture refluxed to provide the intermediate shown, in a yield of 40%. The conditions for step (iii) were, mixing p-carborane, and butyl lithium in ether with copper(I) chloride at reflux to provide the intermediate in 72% yield. For step (iv), the intermediate from step (ii) was reacted with butyl lithium in ether at 0° C. and exposed to CO$_2$ and cooled to −80° C., to provide BSPD in 95% yield. For step (v), the intermediate of step (iii) was mixed with methyl lithium in ether and exposed to CO$_2$ and cooled from 0° C. to −80° C. to provide p-bis-CDC in 95% yield.

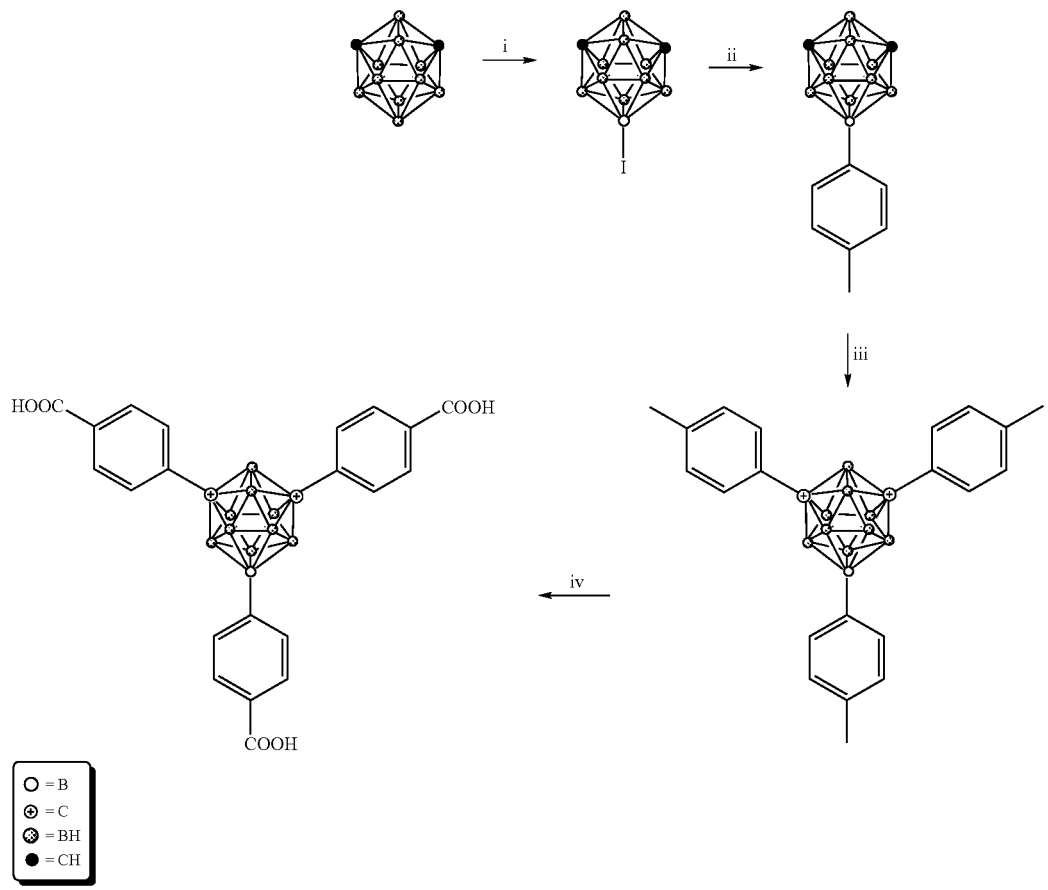

The CB ligand of Scheme 5, B3CB, is prepared as follows. The carborane is reacted with iodine and aluminum chloride in methylene chloride to provide the intermediate after step (i). Then, a coupling reaction is performed with the intermediate, magnesium, 4-iodo toluene, in the presence of $PdCl_2$ $(PPh_3)_2$ at reflux in ether. For step (iii), the intermediate from step (ii) is reacted with butyl lithium in ether with copper chloride at reflux to provide the tris(toluene) intermediate. Next, for step (iv), the tris(toluene) intermediate is reacted with sulfuric acid and chromium oxide in acetone to provide the CB ligand B3CB.

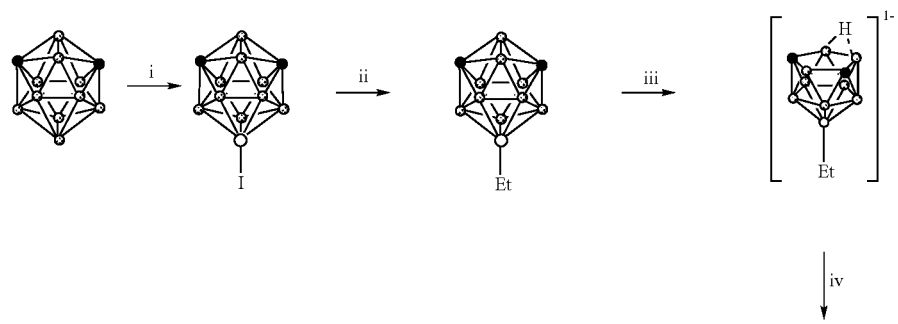

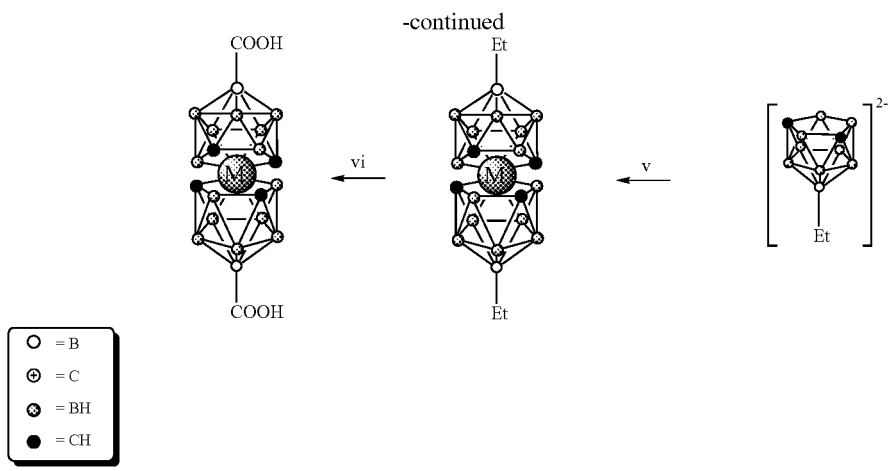

○ = B
⊕ = C
⊗ = BH
● = CH

The synthesis of the metallo-(bis)dicarbollide CB (MCB2) ligand shown above proceeds as follows. M stands for any metal capable of coordinating to the intermediate after step (iv), e.g., nickel, copper, cobalt, iron, or zinc. The conditions for step (i) are exposing the carborane to iodine and aluminum chloride in methylene chloride to form the iodide intermediate. Next, for step (ii) the intermediate is reacted with methyl magnesium bromide and Pd(PPh$_3$)$_2$Cl$_2$ in ether at reflux. The ethyl intermediate is then treated with tetrabutylammonium fluoride (TBAF) at reflux in THF to provide a singly deprotonated intermediate which is then reacted immediately with sodium hydride to provide the doubly deprotonated intermediate. Coordination with a metal ion, e.g., Ni, Co, Cu, Fe, Zn, by mixing with the appropriate metal salt provides the intermediate after step (v). Lastly, the ethyl group is oxidized to a carboxylate by treatment with CrO$_3$ and H$_2$SO$_4$ in acetone.

The MOFs based upon these CB ligands are prepared as follows. The ligand is mixed with the corresponding metal salt (a transition metal or lanthanide) in a molar proportion of 1:n, where n is greater than or equal to 1 in an organic solvent or mixture of organic solvents, such as dimethylformamide, diethylformamide, ethanol, isopropanol, methanol, butanol, or pyridine. The mixture is reacted until crystalline material is formed. Then, the solvent is decanted and the resulting CB-MOF is collected and washed several times with organic solvent to afford the CB-MOF material. The CB-MOF can then be further modified by removing the coordinated solvent molecules under elevated temperature and reduced pressure. Confirmation of removal of all solvent molecules from the CB-MOF can be confirmed via elemental analysis.

For gas sorption applications, the CB-MOF is evacuated at 25-400° C., under vacuum for about 1 to 48 hours to afford activated corresponding CB-MOF materials. Alternatively, activation can proceed via soaking the CB-MOF in a low boiling solvent, such as chloroform, dichloromethane, or acetone for about 1 to 48 hours. This soaking is followed by vacuum evacuation of the low boiling solvent. In activated form, the CB-MOF exhibits a high surface area (e.g., about 150-1500 m$^2$/g and up to about 4000 m$^2$/g).

What is claimed is:

1. A metal-organic framework (MOF) comprising a polymeric crystalline structure of Zn$_3$(OH)(p-CDC)$_{2.5}$L$_m$, wherein p-CDC is 1,12-dihydroxycarbonyl-1,12-dicarba-closo-dodecaborane, L is a solvent, and m is an integer from 0 to 4.

2. The MOF of claim 1, wherein m is different from 0 and at least one L is diethylformamide.

3. The MOF of claim 2, wherein m is different from 0 or 1 and each L is diethylformamide.

4. The MOF of claim 1, wherein m is 2.

5. The MOF of claim 1, wherein m is 4.

6. The MOF of claim 1 having a pore size of about 4 to about 11 Å.

7. The MOF of claim 6, wherein the pore size is about 4.5 to about 9.5 Å.

8. The MOF of claim 1 having a hydrogen gas uptake of about 0.5 wt % to about 2.4 wt % at 77 K and 1 atm.

9. The MOF of claim 8, wherein the H$_2$ uptake is about 1.3 wt % to about 2.1 wt %.

10. A composition comprising the MOF of claim 1 and one or more of a binder, an organic viscosity-enhancing compound, and a liquid.

11. The composition of claim 10, wherein the binder is selected from the group consisting of silica, an oxide of magnesium, an oxide of beryllium, a clay, and mixtures thereof.

12. The composition of claim 10, wherein the organic viscosity-enhancing compound is selected from the group consisting of cellulose, starch, polyacrylate, polymethacrylate, polyvinyl alcohol, polyvinylpyrrolidone, polyisobutene, polytetrahydrofuran, and mixtures thereof.

13. The composition of claim 10, wherein the liquid is selected from the group consisting of water, methanol, ethanol, propanol, n-butanol, isobutanol, tert-butanol, and mixtures thereof.

14. A method of storing a gas comprising exposing a gas to a MOF of claim 1 under conditions sufficient for the MOF to uptake the gas.

15. The method of claim 14, wherein the MOF uptakes the gas at about 0.5 wt % to about 2.5 wt % at 77 K and 1 atm.

16. The method of claim 14, wherein the gas is hydrogen.

17. A metal-organic framework (MOF) comprising a polymeric crystalline structure of a metal and a carborane ligand or an icosohedral borane ligand, and optionally a solvent.

18. The MOF of claim 17 substantially free of a solvent.

19. The MOF of claim 17, wherein the metal is selected from the group consisting of Mg$^{2+}$, Ca$^{2+}$, Sr$^{2+}$, Ba$^{2+}$, Sc$^{3+}$, Y$^{3+}$, Ti$^{4+}$, Zr$^{4+}$, Hf$^{4+}$, V$^{4+}$, V$^{3+}$, Nb$^{3+}$, Ta$^{3+}$, Cr$^{3+}$, Mo$^{3+}$, W$^{3+}$, Mn$^{3+}$, Mn$^{2+}$, Re$^{3+}$, Re$^{2+}$, Fe$^{3+}$, Fe$^{2+}$, Ru$^{3+}$, Ru$^{2+}$, Os$^{3+}$, Os$^{2+}$, Co$^{3+}$, Rh$^{2+}$, Rh$^+$, Ir$^{2+}$Ir$^+$, Ni$^{2+}$, Ni$^+$, Pd$^{2+}$, Pd$^+$, Pt$^{2+}$, Pt$^+$, Cu$^{2+}$, Cu$^+$, Ag$^+$, Au$^+$, Zn$^{2+}$, Cd$^{2+}$, Hg$^{2+}$, Al$^{3+}$, Ga$^{3+}$, In$^{3+}$, Tl$^{3+}$, Si$^{4+}$, Ge$^{4+}$, Ge$^{2+}$, Sn$^{4+}$, Sn$^{2+}$, Pb$^{4+}$, Pb$^{2+}$, As$^{5+}$, As$^{3+}$, As$^{+}$, Sb$^{5+}$, Sb$^{3+}$, Sb$^{+}$, Bi$^{5+}$, Bi$^{3+}$, Bi$^{+}$, and mixtures thereof.

20. The MOF of claim 17, wherein the carborane ligand is selected from the group consisting of

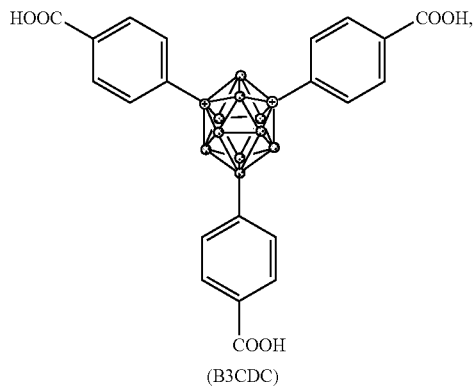

(B3CDC)

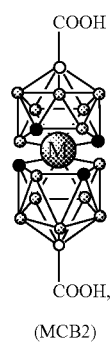

(MCB2)

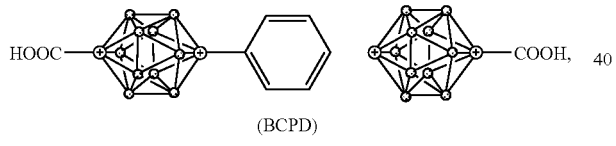

(BCPD)

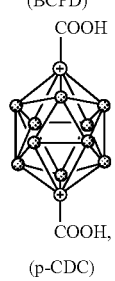

(p-CDC)

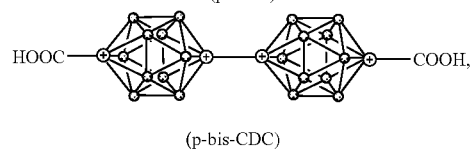

(p-bis-CDC)

and
mixtures thereof,
wherein M is selected from the group consisting of nickel, copper, cobalt, iron, and zinc.

21. The MOF of claim 17, wherein the metal comprises zinc, nickel, cobalt, manganese, or a mixture thereof.

22. The MOF of claim 17, wherein the carborane ligand comprises

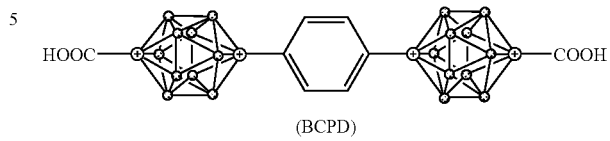

(BCPD)

and the metal comprises zinc.

23. The MOF of claim 22 comprising Zn$_2$(BCPD)$_2$L$_m$, wherein L is a solvent and m is an integer from 0 to 4.

24. The MOF of claim 17, wherein the carborane ligand comprises

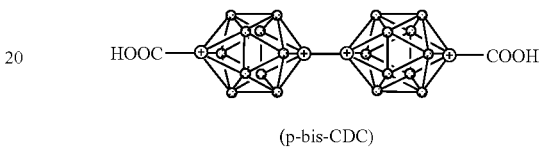

(p-bis-CDC)

and the metal comprises zinc.

25. The MOF of claim 24 comprising Zn$_3$(OH)(p-bis-CDC)$_{2.5}$L$_m$, wherein L is a solvent and m is an integer from 0 to 4.

26. The MOF of claim 17, wherein the carborane ligand comprises

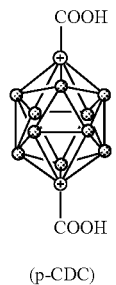

(p-CDC)

and the metal comprises cobalt.

27. The MOF of claim 26 comprising Co$_4$(OH$_2$)(p-CDC)$_3$L$_m$, wherein L is a solvent and m is an integer from 0 to 4.

28. The MOF of claim 17, wherein the carborane ligand comprises

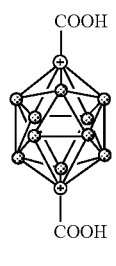

(p-CDC)

and the metal comprises manganese.

29. The MOF of claim 28 comprising Mn(p-CDC)L$_m$, wherein L is a solvent and m is an integer from 0 to 4.

30. The MOF of claim 17 having a surface area of about 100 to about 4000 m$^2$/g.

31. The MOF of claim 30 having a surface area of about 150 to about 1500 m$^2$/g.

32. A method of storing a gas comprising exposing the gas to the MOF of claim 17 under conditions sufficient for the MOF to uptake the gas.

* * * * *

UNITED STATES PATENT AND TRADEMARK OFFICE
CERTIFICATE OF CORRECTION

PATENT NO.        : 7,824,473 B2                          Page 1 of 1
APPLICATION NO.   : 12/180074
DATED             : November 2, 2010
INVENTOR(S)       : Chad A. Mirkin et al.

It is certified that error appears in the above-identified patent and that said Letters Patent is hereby corrected as shown below:

Col. 1, line 7 should read
   This invention was made with government support under Grant No. DE-FG02-01ER15244 awarded by the Department of Energy and Grant No. W911NF-06-1-0116 awarded by the Army Research Office. The government has certain rights in the invention.

Signed and Sealed this
Twenty-eighth Day of December, 2010

David J. Kappos
*Director of the United States Patent and Trademark Office*